United States Patent
Hagiya

(10) Patent No.: US 7,393,971 B2
(45) Date of Patent: Jul. 1, 2008

(54) METHOD FOR PRODUCING 3,3-DIMETHYL-2-(1-PROPENYL) CYCLOPROPANECARBOXYLATE

(75) Inventor: Koji Hagiya, Ibaraki (JP)

(73) Assignee: Sumitomo Chemical Company, Limited, Tokyo (JP)

(*) Notice: Subject to any disclaimer, the term of this patent is extended or adjusted under 35 U.S.C. 154(b) by 221 days.

(21) Appl. No.: 10/574,908

(22) PCT Filed: Nov. 4, 2004

(86) PCT No.: PCT/JP2004/016703

§ 371 (c)(1),
(2), (4) Date: Apr. 6, 2006

(87) PCT Pub. No.: WO2005/044776

PCT Pub. Date: May 19, 2005

(65) Prior Publication Data

US 2007/0078278 A1    Apr. 5, 2007

(30) Foreign Application Priority Data

Nov. 7, 2003    (JP)    ............... 2003-378098

(51) Int. Cl.
*C07C 69/74* (2006.01)
(52) U.S. Cl. .................................... 560/124
(58) Field of Classification Search ............ None
See application file for complete search history.

(56) References Cited

U.S. PATENT DOCUMENTS

| | | | |
|---|---|---|---|
| 2,662,914 A | 12/1953 | Robeson et al. | |
| 5,164,497 A | 11/1992 | King et al. | |
| 2001/0014755 A1 | 8/2001 | Yoshiyama | |

FOREIGN PATENT DOCUMENTS

| | | |
|---|---|---|
| GB | 1571432 | 7/1980 |
| GB | 1571433 | 7/1980 |
| GB | 1571434 | 7/1980 |
| JP | 49-66660 A | 6/1974 |
| JP | 4966660 * | 6/1974 |
| JP | 52-100451 A | 8/1977 |
| JP | 56-40616 A | 4/1981 |
| JP | 4-279540 A | 10/1992 |
| JP | 2001-261618 A | 9/2001 |
| WO | WO-00/35850 A1 | 6/2000 |

OTHER PUBLICATIONS

Chem. Soc., (C), 2739 (1971).*
Bulletin de la Societe Chimique de France (1967), (4), 1411.*
English language translation of Staudinger et al., Helvetica Chimica Acta, vol. 7, pp. 201-211, (1924).
Staudinger et al., Helvetica Chimica Acta, vol. 7, pp. 201-211, (1924).
Sovish, R., J. of Organic Chem., vol. 24, pp. 1345-1347, (1959).
Crombie et al., J. Chem. Soc., Sec. C, pp. 2739-2743, (1971).
Darensbourg et al., Inorg. Chem., vol. 31, pp. 3951-3955, (1992).
Cohen et al., J. Amer. Chem. Soc., vol. 92, pp. 3189-3190, (1970).
Pattenden, Gerald et al., J. Chem. Soc. C., 1971, (16), 2739-2743: Chemical abstracts, vol. 75, No. 15, Oct. 11, 1971, p. 286, the abstract No. 98205s.

* cited by examiner

*Primary Examiner*—Karl J Puttlitz
(74) *Attorney, Agent, or Firm*—Birch, Stewart, Kolasch & Birch, LLP

(57) ABSTRACT

A method for producing 3,3-dimethyl-2-(1-propenyl)cyclopropanecarboxylate represented by the formula (2):

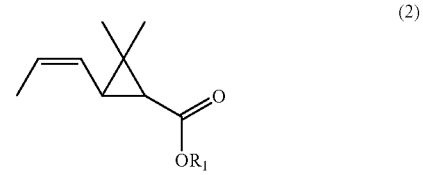

(2)

wherein $R_1$ represent an optionally substituted alkyl group, an optionally substituted aryl group or an optionally substituted aralkyl group, which comprises a 3,3-dimethyl-2-(2-carboxy-1-propenyl)cyclopropanecarboxylate represented by the formula (1):

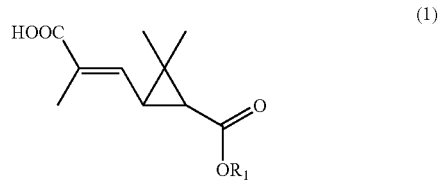

(1)

wherein $R_1$ is as described above, is brought into contact with a copper compound and a nitrogen-containing aromatic compound, is provided.

15 Claims, No Drawings

METHOD FOR PRODUCING 3,3-DIMETHYL-2-(1-PROPENYL) CYCLOPROPANECARBOXYLATE

TECHNICAL FIELD

The present invention relates to a method for producing a 3,3-dimethyl-2-(1-propenyl)cyclopropanecarboxylate.

BACKGROUND ART 3,3-dimethyl-2-(1-propenyl)cyclopropanecarboxylic acid and the ester thereof are important compounds as acidic parts of household agents for epidemic prevention (e.g. JP 54-3933 B). As the method for producing them, a method of using decarboxylation reaction has been known, and for example, 3,3-dimethyl-2-(1-propenyl)cyclopropanecarboxylic acid can be obtained by heating 3,3-dimethyl-2-(2-carboxy-1-propenyl)cyclopropanecarboxylic acid in the absence of a solvent (e.g. J. Chem. Soc., (C), 2739 (1971)). However, this reaction was not enough for industrial method because of the low selectivity.

DISCLOSURE OF THE INVENTION

According to the method of the present invention, a decarboxylation reaction of a 3,3-dimethyl-2-(2-carboxy-1-propenyl)cyclopropanecarboxylate is proceeded with a good selectivity and it is possible to produce the desirable 3,3-dimethyl-2-(1-propenyl)cyclopropanecarboxylate industrially advantageously.

That is, the present invention provides a method for producing a 3,3-dimethyl-2-(1-propenyl)cyclopropanecarboxylate represented by the formula (2):

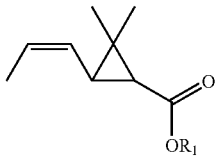

(2)

wherein $R_1$ represents an optionally substituted alkyl group, an optionally substituted aryl group or an optionally substituted aralkyl group, which comprises a 3,3-dimethyl-2-(2-carboxy-1-propenyl) cyclopropanecarboxylate represented by the formula (1):

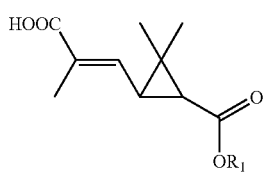

(1)

wherein $R_1$ is as described above, is brought into contact with a copper compound and a nitrogen-containing aromatic compound.

BEST MODE FOR CARRYING OUT THE PRESENT INVENTION

The present invention will be illustrated below in detail.

The method for producing a 3,3-dimethyl-2-(2-carboxy-1-propenyl)cyclopropanecarboxylate represented by the formula (1) (hereinafter, described as the pyrethrate ester (1)) is not particularly limited and for example, it can be obtained in a high yield by reacting a 3,3-dimethyl-2-formylcyclopropanecarboxylate with a dicarboxylic acid derivative such as methylmalonic acid in the presence of a secondary amine according to the description in JP 2000-256253 A.

The substituent $R_1$ of the pyrethrate ester (1) will be illustrated below.

Examples of the alkyl groups represented by $R_1$ include straight chain, branched chain or cyclic alkyl groups having 1 to 20 carbon atoms such as a methyl, ethyl, n-propyl, isopropyl, n-butyl, isobutyl, sec-butyl, tert-butyl, n-pentyl, n-decyl, undecyl, dodecyl, tridecyl, tetradecyl, pentadecyl, hexadecyl, heptadecyl, octadecyl, nonadecyl, dodecyl, cyclopropyl, 2,2-dimethylcyclopropyl, cyclopentyl, cyclohexyl and menthyl group.

Examples of the substituents of the above-mentioned alkyl groups include optionally substituted alkoxy groups having 1 to 20 carbon atoms such as a methoxy, ethoxy, n-propoxy, isopropoxy, n-butoxy, isobutoxy, sec-butoxy, tert-butoxy and trifluoromethoxy group;

optionally substituted aryloxy groups having 6 to 20 carbon atoms such as a phenoxy, 2-methylphenoxy, 4-chlorophenoxy, 4-methylphenoxy, 4-methoxyphenoxy and 3-phenoxyphenoxy group;

optionally substituted aralkyloxy groups having 7 to 20 carbon atoms such as a benzyloxy, 4-chlorobenzyloxy, 4-methylbenzyloxy, 4-methoxybenzyloxy, 3-phenoxybenzyloxy, 2,3,5,6-tetrafluorobenzyloxy, 2,3,5,6-tetrafluoro-4-methylbenzyloxy, 2,3,5,6-tetrafluoro-4-methoxybezyloxy and 2,3,5,6-tetrafluoro-4-methoxymethylbenzyloxy group;

halogen atoms such as a fluorine, chlorine, bromine and iodine atom;

optionally substituted acyl groups having 2 to 20 carbon atoms such as an acetyl and ethylcarbonyl group;

optionally substituted arylcarbonyl groups having 7 to 20 carbon atoms such as a phenylcarbonyl, 2-methylphenylcarbonyl, 4-chlorophenylcarbonyl, 4-methylphenylcarbonyl and 4-methoxyphenylcarbonyl group;

optionally substituted aralkylcarbonyl groups having 8 to 20 carbon atoms such as a benzylcarbonyl, 4-chlorobenzylcarbonyl, 4-methylbenzylcarbonyl and 4-methoxybenzylcarbonyl group;

optionally substituted alkoxycarbonyl groups having 2 to 20 carbon atoms such as a methoxycarbonyl, ethoxycarbonyl, tert-butoxycarbonyl and trifluoromethoxycarbonyl group;

optionally substituted aryloxycarbonyl groups having 7 to 20 carbon atoms such as a phenoxycarbonyl, 2-methylphenoxycarbonyl, 4-chlorophenoxycarbonyl, 4-methylphenoxycarbonyl and 4-methoxyphenoxycarbonyl group;

optionally substituted aralkyloxycarbonyl groups having 8 to 20 carbon atoms such as a benzyloxycarbonyl, 4-chlorobenzyloxycarbonyl, 4-methylbenzyloxycarbonyl and 4-methoxybenzyloxycarbonyl group; and a carboxyl group.

Examples of the alkyl groups substituted with the substituent or substituents include a chloromethyl, fluoromethyl, methoxymethyl, ethoxymethyl, methoxyethyl and methoxycarbonylmethyl group.

Examples of the aryl groups include aryl groups having 6 to 20 carbon atoms such as a phenyl and naphthyl group. The aryl group may be substituted with a substituent or substituents such as the above-mentioned optionally substituted alkyl group; the above-mentioned aryl group; the optionally substituted aralkyl group described below; an optionally substituted alkoxy group having 1 to 20 carbon atoms such as a methoxy, ethoxy, n-propoxy, isopropoxy, n-butoxy, isobutoxy, sec-butoxy, tert-butoxy and trifluoromethoxy group; an optionally substituted aryloxy group having 6 to 20 carbon atoms such as a phenoxy, 2-methylphenoxy, 4-chlorophenoxy, 4-methylphenoxy, 4-methoxyphenoxy and 3-phenoxyphenoxy group; an optionally substituted aralkyloxy group having 7 to 20 carbon atoms such as a benzyloxy, 4-chlorobenzyloxy, 4-methylbenzyloxy, 4-methoxybenzyloxy, 3-phenoxybenzyloxy, 2,3,5,6-tetrafluorobenzyloxy, 2,3,5,6-tetrafluoro-4-methylbenzyloxy, 2,3,5,6-tetrafluoro-4-methoxybenzyloxy and 2,3,5,6-tetrafluoro-4-methoxymethylbenzyloxy group; and a halogen atom such as a fluorine, chlorine, bromine and iodine atom.

Examples of the optionally substituted aryl groups include a phenyl, naphthyl, 2-methylphenyl, 4-chlorophenyl, 4-methylphenyl, 4-methoxyphenyl and 3-phenoxyphenyl group.

Examples of the aralkyl groups include aralkyl groups having 7 to 20 carbon atoms such as a benzyl and naphthylmethyl group.

The aralkyl group may be substituted with a substituent or substituents such as the above-mentioned optionally substituted alkyl group; the above-mentioned optionally substituted aryl group; the above-mentioned aralkyl group; an optionally substituted alkoxy group having 1 to 20 carbon atoms such as a methoxy, ethoxy, n-propoxy, isopropoxy, n-butoxy, isobutoxy, sec-butoxy, tert-butoxy and trifluoromethoxy group; an optionally substituted aryloxy group having 6 to 20 carbon atoms such as a phenoxy, 2-methylphenoxy, 4-chlorophenoxy, 4-methylphenoxy, 4-methoxyphenoxy and 3-phenoxyphenoxy group; an optionally substituted aralkyloxy group having 7 to 20 carbon atoms such as a benzyloxy, 4-chlorobenzyloxy, 4-methylbenzyloxy, 4-methoxybenzyloxy, 3-phenoxybenzyloxy, 2,3,5,6-tetrafluorobenzyloxy, 2,3,5,6-tetrafluoro-4-methylbenzyloxy, 2,3,5,6-tetrafluoro-4-methoxybenzyloxy and 2,3,5,6-tetrafluoro-4-methoxymethylbenzyloxy group; and a halogen atom such as a fluorine, chlorine, bromine and iodine atom.

As the optionally substituted aralkyl groups having 7 to 20 carbon atoms, benzyl groups substituted with a substituent or substituents selected from a halogen atom, a methyl group, a methoxy group, a methoxymethyl group and a phenoxy group are preferably exemplified. Specific examples thereof include a 4-chlorobenzyl, 4-methylbenzyl, 4-methoxybenzyl, 3-phenoxybenzyl, 2,3,5,6-tetrafluorobenzyl, 2,3,5,6-tetrafluoro-4-methylbenzyl, 2,3,5,6-tetrafluoro-4-methoxybenzyl and 2,3,5,6-tetrafluoro-4-methoxymethylbenzyl group.

As the groups represented by $R_1$, straight chain, branched chain or cyclic alkyl groups having 1 to 20 carbon atoms and benzyl groups substituted with a substituent or substituents selected from a halogen atom, a methyl group, a methoxy group, a methoxymethyl group and a phenoxy group are preferably exemplified.

Examples of the pyrethrate ester (1) include methyl 3,3-dimethyl-2-(2-carboxy-1-propenyl)cyclopropanecarboxylate, ethyl 3,3-dimethyl-2-(2-carboxy-1-propenyl)cyclopropanecarboxylate, isopropyl 3,3-dimethyl-2-(2-carboxy-1-propenyl)cyclopropanecarboxylate, tert-butyl 3,3-dimethyl-2-(2-carboxy-1-propenyl)cyclopropanecarboxylate, cyclohexyl 3,3-dimethyl-2-(2-carboxy-1-propenyl)cyclopropanecarboxylate, menthyl 3,3-dimethyl-2-(2-carboxy-1-propenyl)cyclopropanecarboxylate, benzyl 3,3-dimethyl-2-(2-carboxy-1-propenyl)cyclopropanecarboxylate, 4-chlorobenzyl 3,3-dimethyl-2-(2-carboxy-1-propenyl)cyclopropanecarboxylate, 2,3,5,6-tetrafluorobenzyl 3,3-dimethyl-2-(2-carboxy-1-propenyl)cyclopropanecarboxylate, 2,3,5,6,-tetrafluoro-4-methylbenzyl 3,3-dimethyl-2-(2-carboxy-1-propenyl)cyclopropanecarboxylate, 2,3,5,6-tetrafluoro-4-methoxybenzyl 3,3-dimethyl-2-(2-carboxy-1-propenyl)cyclopropanecarboxylate, 2,3,5,6-tetrafluoro-4-methoxymethylbenzyl 3,3-dimethyl-2-(2-carboxy-1-propenyl)cyclopropanecarboxylate and 3-phenoxybenzyl 3,3-dimethyl-2-(2-carboxy-1-propenyl)cyclopropanecarboxylate.

The prethrate ester (1) has two asymmetric carbon atoms and the optically active isomers exist. The optically active isomer of the compound of the formula (1) alone or a mixture thereof may be used. For example, it is possible to produce an optically active 3,3-dimethyl-2-(1-propenyl)cyclopropanecarboxylate represented by the formula (5):

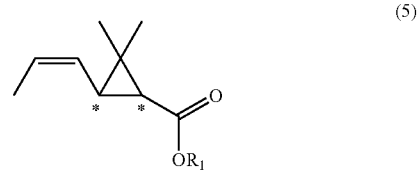

(5)

wherein $R_1$ is the same as the above and * represents an asymmetric carbon atom, by carrying out the reaction using an optically active 3,3-dimethyl-2-(2-carboxy-1-propenyl)cyclopropanecarboxylate represented by the formula (4):

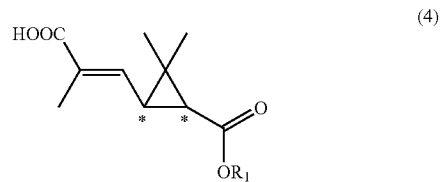

(4)

wherein $R_1$ and * are the same as the above, which is an optical isomer of the 3,3-dimethyl-2-(2-carboxy-1-propenyl)cyclopropanecarboxylate of the formula (1) alone or a mixture thereof.

Examples of the copper compounds used in the present invention include a monovalent copper compound such as copper(I) oxide, copper(I) acetate and copper(I) hydroxide; a copper compound obtained by reacting a divalent copper compound such as copper(II) oxide, copper(II) acetate, copper(II) hydroxide and copper(II) naphthenate with a reducing agent such as hydrogen and hydrazine; and a copper compound obtained by reacting a copper metal with a oxidizing agent such as oxygen and hydrogen peroxide. These copper compounds may be used alone and some of them may be mixed to use.

When the divalent copper compound is reacted with the reducing agent or the copper metal is reacted with the oxidizing agent, the procedure may be carried out previously and simultaneously in the decarboxylation reaction system. When the copper metal is used, the copper metal of which particle size is as small as possible is used preferably to improve the reactivity.

When the procedure is carried out previously, the copper compound obtained may be isolated to use in the decarboxylation reaction and the solution or slurry containing it may be used as it is. The above-mentioned "the procedure is carried out simultaneously in the decarboxylation reaction system" means, for example, in the case that the pyrethrate ester (1), a nitrogen-containing aromatic compound, the copper metal and the oxidizing agent are charged simultaneously and heated thereof.

When the non-bidentate nitrogen-containing aromatic compound described below is used, the amount of the copper compound to be used is preferably about 0.1 to 2 moles, more preferably about 0.5 to 1.5 moles per 1 mole of the pyrethrate ester (1). When the bidentate nitrogen-containing aromatic compound described below is used, the amount of the copper compound to be used may be a catalytic amount and is preferably about 0.01 to 0.5 mole, more preferably about 0.05 to 0.3 mole per 1 mole of the pyrethrate ester (1).

Examples of the nitrogen-containing aromatic compounds used in the present invention include compounds having a nitrogen-containing aromatic ring containing a nitrogen atom as the constituting element such as a pyridine and quinoline ring, in more detail, non-bidentate nitrogen-containing aromatic compounds (for example, the nitrogen-containing aromatic compound selected from quinoline, 2-chloroquinoline, 4-nitroquinoline, pyridine, collidine, methyl nicotinate, isoquinoline and the like), and bidentate nitrogen-containing compounds represented by the formula (3):

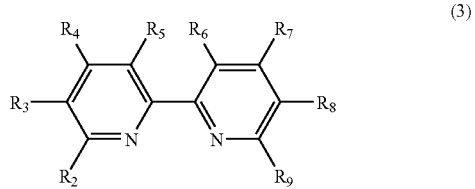

wherein $R_2$, $R_3$, $R_4$, $R_5$, $R_6$, $R_7$, $R_8$ and $R_9$ are the same or different, and independently represent a hydrogen atom, an optionally substituted alkyl group, an optionally substituted alkoxy group, an optionally substituted aryl group, an optionally substituted aryloxy group, an optionally substituted aralkyl group, an optionally substituted aralkyloxy group, an optionally substituted alkenyl group, a halogen atom, a nitro group, a cyano group, an optionally substituted acyl group, a sulfo group or an optionally substituted alkoxycarbonyl group; provided that, $R_2$ and $R_3$, $R_3$ and $R_4$, $R_4$ and $R_5$, $R_5$ and $R_6$, $R_6$ and $R_7$, $R_7$ and $R_8$, or $R_8$ and $R_9$ may be bonded to form a part of the ring structure containing the aromatic ring.

The nitrogen-containing aromatic ring of the non-bidentate nitrogen-containing aromatic compound may have a substituent or substituents. Examples of the substituents include the above-mentioned optionally substituted alkyl groups; the above-mentioned optionally substituted aryl groups; the above-mentioned optionally substituted aralkyl groups; optionally substituted alkoxy groups such as a methoxy, ethoxy, n-propoxy, isopropoxy, n-butoxy, isobutoxy, sec-butoxy, tert-butoxy and trifluoromethoxy group; optionally substituted aryloxy groups such as a phenoxy, 2-methylphenoxy, 4-chlorophenoxy, 4-methylphenoxy, 4-methoxyphenoxy and 3-phenoxyphenoxy group; optionally substituted aralkyloxy groups such as a benzyloxy, 4-chlorobenzyloxy, 4-methylbenzyloxy, 4-methoxybenzyloxy and 3-phenoxybenzyloxy group; optionally substituted acyl groups such as a acetyl and ethylcarbonyl group; optionally substituted alkoxycarbonyl groups such as a methoxycarbonyl, ethoxycarbonyl, tert-butoxycarbonyl and trifluoromethoxycarbonyl group; optionally substituted aryloxycarbonyl groups such as a phenoxycarbonyl, 2-methylphenoxycarbonyl, 4-chlorophenoxycarbonyl, 4-methylphenoxycarbonyl and 4-methoxyphenoxycarbonyl group; optionally substituted carbaralkyloxy groups such as a benzyloxycarbonyl, 4-chlorobenzyloxycarbonyl, 4-methylbenzyloxycarbonyl and 4-methoxybenzyloxycarbonyl group; halogen atoms such as a fluorine, chlorine, bromine and iodine atom; a sulfo group; a cyano group; a hydroxyl group; a nitro group; and an amino group. Among them, the neighboring substituents may be bonded to form a ring containing the carbon atom to which they are bonded.

Examples of the non-bidentate nitrogen-containing aromatic compounds include quinoline, 2-chloroquinoline, 4-nitroquinoline, pyridine, collidine, methyl nicotinate and isoquinoline like the above and quinoline is preferably used.

The amount of the non-bidentate nitrogen-containing aromatic compound to be used is usually 0.5 mole or more per 1 mole of the pyrethrate ester (1). There is no upper limit particularly and large excess thereof may be used also to serve as the solvent.

As $R_2$ to $R_9$ which are substituents of the bidentate nitrogen-containing compound represented by the formula (3) used in the present invention, a hydrogen atom, the optionally substituted alkyl group described above as the group represented by $R_1$, the optionally substituted alkenyl group described below, the above-mentioned optionally substituted aryl group, the above-mentioned optionally substituted aralkyl group, the above-mentioned optionally substituted alkoxy group, the above-mentioned optionally substituted aryloxy group, the above-mentioned optionally substituted aralkyloxy group, a halogen atom, a nitro group, a cyano group, the above-mentioned optionally substituted acyl group and the above-mentioned optionally substituted alkoxycarbonyl group are exemplified.

Examples of the optionally substituted alkenyl groups include alkenyl groups having 2 to 12 carbon atoms such as an ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 1-pentenyl, 2-pentenyl, 3-pentenyl, 1-hexenyl, 1-decenyl, 2-cyclopentenyl and 2-cyclohexenyl group, and those in which one or two or more hydrogen atoms are substituted with a substituent or substituents such as the alkoxy group described below, the aryloxy group, the aralkyloxy group, the halogen atom and the acyl group. Examples of the alkenyl groups substituted with the substituent or substituents include a chlorovinyl, fluoropropenyl, trifluorobutenyl, methoxypropenyl and phenoxybutenyl group. The bidentate nitrogen-containing compounds include 1,10-phenanthroline compounds formed by bonding $R_5$ and $R_6$ together to represent a condensed benzene ring and the other 2,2'-bipyridyl compounds.

As the bidentate nitrogen-containing compounds, 2,2'-bipyridyl and 1,10-phenanthroline which may be substituted with a methyl group, a methoxy group, a benzyl group, a benzyloxy group, a phenyl group, a phenoxy group, a cyano group, a methoxycarbonyl group, an acetyl group, a sulfo group, a halogen atom or a nitro group are preferable.

Specific examples of the bidentate nitrogen-containing compounds include bipyridyl compounds such as 2,2'-bipyridyl, 5,5'-dicyano-2,2'-bipyridyl and 4,4'-dibenzyl-2,2'-bipyridyl; and 1,10-phenanthroline compounds such as 1,10-phenanthroline, 4,7-diphenyl-1,10-phenanthroline, 3,4,7,8-tetramethyl-1,10-phenanthroline, 4,7-dimethoxy-1,10-phenanthroline, 4,7-diphenoxy-1,10-phenanthroline, 4,7-dibenzyloxy-1,10-phenanthroline, 3,8-dibromo-1,10-phenanthroline, 3,8-dichloro-1,10-phenanthroline, 4,7- dinitro-1,10-phenanthroline, 2,9-dicarbomethoxy-1,10-phenanthroline, 2-acetyl-1,10-phenanthroline, 1,10-phenanthroline-4,7-disulfonic acid and benzo[f][1,10]-phenanthroline. The 1,10-phenanthroline compounds are preferably used.

The amount of the bidentate nitrogen-containing compound to be used may be a catalytic amount and preferably about 0.01 to 0.5 mole, more preferably about 0.05 to 0.3 mole per 1 mole of the pyrethrate ester (1). As above, it is possible to reduce the amount of the copper compound and the nitrogen-containing compound until the catalytic amount by using the bidentate nitrogen-containing compound as the nitrogen-containing aromatic compound.

The above-mentioned reaction may be carried out in the presence of an organic solvent. When the bidentate nitrogen-containing compound is used, it is preferably carried out in the presence of the organic solvent. When the organic solvent is used, the organic solvent is not limited in so far as it is not prevent from the reaction. Examples of the organic solvents include halogenated hydrocarbons such as chlorobenzene, o-dichlorobenzene and m-dichlorobenzene; aromatic hydrocarbons such as benzene, toluene and nitrobenzene; and aliphatic hydrocarbons such as n-decane, dodecane and tetradecane. Preferred are nitrogen-containing aromatic compounds such as quinoline, 2-chloroquinoline, 4-nitroquinoline, pyridine, collidine, methyl nicotinate and isoquinoline. The amount thereof is usually about 0.5 to 100 parts by weight per 1 part by weight of the pyrethrate ester (1).

In the present invention, it is possible to conduct the reaction more efficiently by adding aluminum oxide thereto and carrying out in the presence of aluminum oxide. As aluminum oxide, any of γ-typed and a-typed aluminum oxide can be used. Any of an acidic, neutral and basic aluminum oxide can be used and the basic to neutral alumina is preferred. The amount thereof is not limited particularly and usually about 0.1 to 2 parts by weight per 1 part by weight of the pyrethrate ester (1).

The present reaction may be carried out by mixing the pyrethrate ester (1), the copper compound, the nitrogen-containing compound, the solvent and if necessary aluminum oxide, and the mixing order is not limited particularly. For example, after mixing them at once, the resulting mixture may be heated to the reaction temperature, or the pyrethrate ester (1) may be added to the mixture obtained by mixing the copper compound, the nitrogen-containing compound, the solvent and if necessary aluminum oxide and controlled at the reaction temperature.

The reaction temperature is usually the range of about 150° C. to 230° C.

The reaction is usually carried out under ordinary pressure and may be carried out under pressurized condition or reduced pressure condition.

The congress of the reaction can be confirmed by a conventional analytical means such as gas chromatography, high-performance liquid chromatography, thin layer chromatography, NMR and IR, and the reaction can be finished at the point of confirming the disappearing the pyrethrate ester (1).

After completion of the reaction, for example, the desirable 3,3-dimethyl-2-(1-propenyl)cyclopropanecarboxylate can be obtained by, if necessary after filtering the copper compound and aluminum oxide from the reaction mass, distilling off the solvent or concentrating after separating the desirable 3,3-dimethyl-2-(1-propenyl)cyclopropanecarboxylate and the nitrogen-containing aromatic compound by adding an aqueous acidic solution and if necessary a water-separable solvent to carry out extracting treatment.

The 3,3-dimetyl-2-(1-propenyl)cyclopropanecarboxylate obtained can be further isolated by using a conventional separation means such as distillation and column chromatography. Examples of the water-insoluble organic solvents include halogenated hydrocarbon solvents such as dichloromethane, chloroform and chlorobenzene; ether solvents such as diethyl ether and methyl tert-butyl ether; and ester solvents such as ethyl acetate. The amount thereof to be used is not particularly limited.

Examples of the 3,3-dimethyl-2-(1-propenyl)cyclopropanecarboxylate represented by the formula (2) obtained include methyl 3,3-dimethyl-2-(1-propenyl)cyclopropanecarboxylate, ethyl 3,3-dimethyl-2-(1-propenyl)cyclopropanecarboxylate, isopropyl 3,3-dimethyl-2-(1-propenyl)cyclopropanecarboxylate, tert-butyl 3,3-dimethyl-2-(1-propenyl)cyclopropanecarboxylate, cyclohexyl 3,3-dimethyl-2-(1-propenyl)cyclopropanecarboxylate, menthyl 3,3-dimethyl-2-(1-propenyl)cyclopropanecarboxylate, benzyl 3,3-dimethyl-2-(1-propenyl)cyclopropanecarboxylate, 4-chlorobenzyl 3,3-dimethyl-2-(1-propenyl)cyclopropanecarboxylate, 2,3,5,6-tetrafluorobenzyl 3,3-dimethyl-2-(1-propenyl)cyclopropanecarboxylate, 2,3,5,6,-tetrafluoro-4-methylbenzyl 3,3-dimethyl-2-(1-propenyl)cyclopropanecarboxylate, 2,3,5,6-tetrafluoro-4-methoxybenzyl 3,3-dimethyl-2-(1-propenyl)cyclopropanecarboxylate, 2,3,5,6-tetrafluoro-4-methoxymethylbenzyl 3,3-dimethyl-2-(1-propenyl)cyclopropanecarboxylate and 3-phenoxybenzyl 3,3-dimethyl-2-(1-propenyl)cyclopropanecarboxylate.

When the optically active isomer is used as the pyrethrate ester (1), 3,3-dimethyl-2-(1-propenyl)cyclopropanecarboxylate compound is usually obtained with almost keeping the optically purity.

EXAMPLES

The present invention will be further illustrated in more detail by Examples. The present invention is not limited to these Examples. The yield and E/Z ratio was calculated based on the results of gas chromatography analysis method (internal standard method). Herein, E/Z ratio means a ratio of configuration of a methyl group and a cyclopropane ring of the double bond moiety. Optically purity was calculated by high performance liquid chromatography (hereinafter, simply referred to as LC) analysis method (area comparison method).

GC Analytical Condition
　　Column: DB-1 (φ 0.25 μm×30 m, Film thickness 1.0 μm)
　　Carrier gas: Helium (Flow rate: 1 m/min.)
　　Split ratio: 1/10, Injection volume of sample: 1 μL
　　Column temperature: 100° C. (0 min.)→180° C. (Warm-up rate: 2° C./min., Keeping time at 180° C.: 0 min.)→300° C. (Warm-up rate: 10° C./min., Keeping time at 300° C.: 15 min.)
　　Injection temperature: 200° C., Detection temperature: 250° C.

LC Analytical Condition
　　Column: SUMICHIRAL OA-2500 (5 μm, φ 4.6 mm×25 cm×2)
　　Mobile phase: n-hexane
　　Flow rate: 0.7 mL/min., Injection amount of sample: 1 μL, Detective wavelength: 220 nm

Example 1

Into a 100 ml flask purged with nitrogen, 70 mg of copper (I) oxide, 2 g of quinoline and 212 mg of methyl 3,3-dimethy-2-(2-carboxy-1-propenyl)cyclopropanecarboxylate were charged and heated to 180° C. in an atmosphere of nitrogen. After stirring at the same temperature for 3 hours, the reaction mixture was cooled and 10 g of 10% aqueous sulfuric acid and 5 g of toluene were added thereto and the resulting mixture was separated to obtain an organic layer containing methyl 3,3-dimethyl-2-(1-propenyl)cyclopropanecarboxylate. The yield of methyl 3,3-dimethyl-2-(1-propenyl)cyclopropanecarboxylate was 69% and E/Z ratio was 5:95.

Example 2

In an atmosphere of air, 65 mg of copper powder, 2 g of quinoline and 212 mg of methyl 3,3-dimethyl-2-(2-carboxy-1-propenyl)cyclopropanecarboxylate were charged into a 100 ml flask and heated to 180° C. in an atmosphere of air. After stirring at the same temperature for 3 hours, the reaction mixture was cooled and 10 g of 10% aqueous sulfuric acid and 5 g of toluene were added thereto and the resulting mixture was separated to obtain an organic layer containing methyl 3,3-dimethyl-2-(1-propenyl)cyclopropanecarboxylate. The yield of methyl 3,3-dimethyl-2-(1-propenyl)cyclopropanecarboxylate was 52% and E/Z ratio was 11:89.

Example 3

Into a 100 ml flask purged with nitrogen, 5 mg of copper(I) oxide, 30 mg of copper powder, 1 g of quinoline and 106 mg of methyl (+)-trans-3,3-dimethy-2-(2-carboxy-1-propenyl)cyclopropanecarboxylate (d-isomer ratio: 95.5%) were charged and heated to 180° C. in an atmosphere of nitrogen. After stirring at the same temperature for 3 hours, the reaction mixture was cooled and 10 g of 10% aqueous sulfuric acid and 5 g of toluene were added thereto and the resulting mixture was separated to obtain an organic layer containing methyl (+)-trans-3,3-dimethyl-2-(1-propenyl)cyclopropanecarboxylate. The yield of methyl 3,3-dimethyl-2-(1-propenyl)cyclopropanecarboxylate was 65% and E/Z ratio was 5:95. The d-isomer ratio, which was total of d-isomer of E-isomer and d-isomer of Z-isomer, was 95.5%.

Comparative Example 1

According to the same manner as that described in Example 2, the yield of methyl 3,3-dimethyl-2-(1-propenyl)cyclopropanecarboxylate was 0.8% and the raw material methyl 3,3-dimethyl-2-(2-carboxy-1-propenyl)cyclopropanecarboxylate was recovered in a yield of 98% except that the reaction was carried out in an atmosphere of nitrogen in a flask purged nitrogen.

Example 4

Into a 100 ml flask purged with nitrogen, 35 mg of copper (I) oxide, 99 mg of 1,10-phenanthroline monohydrate, 2 g of tetradecane and 212 mg of methyl 3,3-dimethy-2-(2-carboxy-1-propenyl)cyclopropanecarboxylate were charged and heated to 180° C. in an atmosphere of nitrogen. After stirring at the same temperature for 2 hours, the reaction mixture was cooled and 10 g of 10% aqueous sulfuric acid and 5 g of toluene were added thereto and the resulting mixture was separated to obtain an organic layer containing methyl 3,3-dimethyl-2-(1-propenyl)cyclopropanecarboxylate. The yield of methyl 3,3-dimethyl-2-(1-propenyl)cyclopropanecarboxylate was 59% and E/Z ratio was 4:96.

Example 5

Into a 100 ml flask purged with nitrogen, 70 mg of copper (I) oxide, 156 mg of 2,2'-bipyridyl, 2 g of tetradecane and 212 mg of methyl 3,3-dimethy-2-(2-carboxy-1-propenyl)cyclopropanecarboxylate were charged and heated to 180° C. in an atmosphere of nitrogen. After stirring at the same temperature for 2 hours, the reaction mixture was cooled and 10 g of 10% aqueous sulfuric acid and 5 g of toluene were added thereto and the resulting mixture was separated to obtain an organic layer containing methyl 3,3-dimethyl-2-(1-propenyl)cyclopropanecarboxylate. The yield of methyl 3,3-dimethyl-2-(1-propenyl)cyclopropanecarboxylate was 61% and E/Z ratio was 7:93.

Example 6

Into a 100 ml flask purged with nitrogen, 5 mg of copper(I) oxide, 30 mg of 1,10-phenanthroline monohydrate, 200 mg of neutral alumina, 2 g of quinoline and 212 mg of methyl 3,3-dimethy-2-(2-carboxy-1-propenyl)cyclopropanecarboxylate were charged and heated to 180° C. in an atmosphere of nitrogen. After stirring at the same temperature for 2 hours, the reaction mixture was cooled and 10 g of 10% aqueous sulfuric acid and 5 g of toluene were added thereto and the resulting mixture was separated to obtain an organic layer containing methyl 3,3-dimethyl-2-(1-propenyl)cyclopropanecarboxylate. The yield of methyl 3,3-dimethyl-2-(1-propenyl)cyclopropanecarboxylate was 71% and E/Z ratio was 2:98.

Example 7

Into a 300 ml flask purged with nitrogen, 200 mg of copper (I) oxide, 1000 mg of 4,7-diphenyl-1,10-phenanthroline, 2 g of neutral alumina and 5 g of quinoline were charged and heated to 180° C. in an atmosphere of nitrogen. 2.12 g of methyl 3,3-dimethy-2-(2-carboxy-1-propenyl)cyclopropanecarboxylate was dissolved in 5 g of quinoline and the solution was added dropwise to this mixture over 4 hours. After adding dropwise, the reaction mixture was stirred at the same temperature for 2 hours and cooled. 50 g of 10% aqueous sulfuric acid and 50 g of toluene were added thereto and the resulting mixture was separated to obtain an organic layer containing methyl 3,3-dimethyl-2-(1-propenyl)cyclopropanecarboxylate. The yield of methyl 3,3-dimethyl-2-(1-propenyl)cyclopropanecarboxylate was 91% and E/Z ratio was 1:99.

Example 8

According to the same manner as that described in Example 7, an organic layer containing methyl 3,3-dimethyl-2-(1-propenyl)cyclopropanecarboxylate was obtained except that the amount of 4,7-diphenyl-1,10-phenanthroline was 100 mg. The yield of methyl 3,3-dimethyl-2-(1-propenyl)cyclopropanecarboxylate was 73% and E/Z ratio was 3:97.

INDUSTRIAL APPLICABILITY

According to the method of the present invention, it is possible to produce a 3,3-dimethyl-2-(1-propenyl)cyclopropanecarboxylate, which is an important compound as an acidic part of household agents for epidemic prevention, efficiently without using reagents which are difficult to handle industrially, expensive reagents or particular reactors, and without producing large amount of waste as by-product.

The invention claimed is:

1. A method for producing 3,3-dimethyl-2-(1-propenyl) cyclopropanecarboxylate represented by the formula (2):

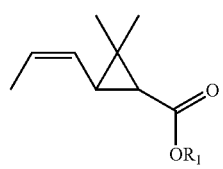

(2)

wherein $R_1$ represent an optionally substituted alkyl group, an optionally substituted aryl group or an optionally substituted aralkyl group, which method comprises contacting a 3,3-dimethyl-2-(2-carboxy-1-propenyl)cyclopropanecarboxylate represented by the formula (1):

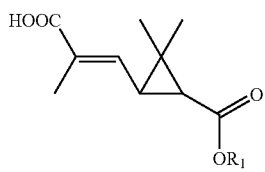

(1)

wherein $R_1$ is as described above,
with a copper compound and a nitrogen-containing aromatic compound.

2. The method for producing according to claim 1, wherein the copper compound is a monovalent copper compound.

3. The method for producing according to claim 1, wherein the copper compound is a copper compound obtained by reacting a divalent copper compound with a reducing agent.

4. The method for producing according to claim 1, wherein the copper compound is a copper compound obtained by reacting copper metal with a oxidizing agent.

5. The method for producing according to any of claims 1 to 4, wherein the nitrogen-containing aromatic compound is quinoline.

6. The method for producing according to any of claims 1 to 4, wherein the nitrogen-containing aromatic compound is a bidentate nitrogen-containing compound represented by the formula (3):

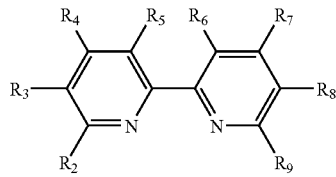

(3)

wherein $R_2$, $R_3$, $R_4$, $R_5$, $R_6$, $R_7$, $R_8$ and $R_9$ are the same or different, and independently represent a hydrogen atom, an optionally substituted alkyl group, an optionally substituted alkoxy group, an optionally substituted aryl group, an optionally substituted aryloxy group, an optionally substituted aralkyl group, an optionally substituted aralkyloxy group, an optionally substituted alkenyl group, a halogen atom, a nitro group, a cyano group, an optionally substituted acyl group, a sulfo group or an optionally substituted alkoxycarbonyl group; provided that, $R_2$ and $R_3$, $R_3$ and $R_4$, $R_4$ and $R_5$, $R_5$ and $R_6$, $R_6$ and $R_7$, $R_7$ and $R_8$, or $R_8$ and $R_9$ may be bonded to form a part of the ring structure containing the aromatic ring, and a solvent is used together.

7. The method for producing according to claim 6, wherein the bidentate nitrogen-containing compound is a 1,10-phenanthroline compound.

8. The method for producing according to claim 6, wherein the solvent is a nitrogen-containing aromatic compound.

9. The method for producing according to claim 8, wherein the solvent is quinoline.

10. The method for producing according to claim 1, wherein the reaction is carried out in the presence of aluminum oxide.

11. The method for producing according to claim 1, wherein the reaction temperature is 1500° C. to 2300° C.

12. The method for producing according to claim 1, which comprises producing an optically active 3,3-dimethyl-2-(1-propenyl)cyclopropanecarboxylate represented by the formula (5):

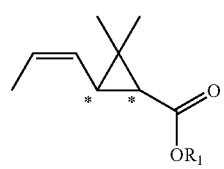

(5)

wherein $R_1$ is the same as the above and * represents an asymmetric carbon atom, by reacting an optically active 3,3-dimethyl-2-(2-carboxy-1-propenyl)cyclopropanecarboxylate represented by the formula (4):

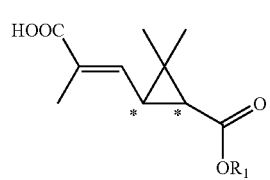

(4)

wherein $R_1$ and * are the same as the above, which is an optical isomer of the 3,3-dimethyl-2-(2-carboxy-1-propenyl)cyclopropanecarboxylate of the formula (1) alone or a mixture thereof.

13. The method for producing according to claim 1, wherein $R_1$ is a straight chain, branched chain or cyclic alkyl group having 1 to 20 carbon atoms, or a benzyl group substituted with a substituents or substituents selected from a halogen atom, a methyl group, a methoxyl group, a methoxymethyl group and a phenoxy group.

14. The method for producing according to claim 6, wherein the bidentate nitrogen-containing compound is 2,2'-bipyridyl or 1,10-phenanthroline which may be substituted with a methyl group, a methoxy group, a benzyl group, a benzyloxy group, a phenyl group, a phenoxy group, a cyano group, a methoxycarbonyl group, an acetyl group, a sulfo group, a halogen atom or a nitro group.

15. The method for producing according to claim 12, wherein the optically active 3,3-dimethyl-2-(2-carboxy-1-propenyl)cyclopropanecarboxylate and the optically active 3,3-dimethyl-2-(1-propenyl)cyclopropanecarboxylate are (+)-trans isomers.

* * * * *